United States Patent
Kobayashi et al.

(10) Patent No.: US 11,951,125 B2
(45) Date of Patent: Apr. 9, 2024

(54) DRUG AND PRODUCTION METHOD THEREFOR

(71) Applicant: OSAKA UNIVERSITY, Osaka (JP)

(72) Inventors: Hikaru Kobayashi, Osaka (JP); Yuki Kobayashi, Osaka (JP); Ryoichi Imamura, Osaka (JP); Norio Nonomura, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 350 days.

(21) Appl. No.: 17/236,891

(22) Filed: Apr. 21, 2021

(65) Prior Publication Data

US 2021/0275578 A1    Sep. 9, 2021

Related U.S. Application Data

(63) Continuation of application No. 16/633,807, filed as application No. PCT/JP2018/025315 on Jul. 4, 2018, now Pat. No. 11,103,527.

(51) Int. Cl.
*A61K 33/00* (2006.01)
*A61K 9/00* (2006.01)
*A61K 9/16* (2006.01)
*A61P 13/12* (2006.01)

(52) U.S. Cl.
CPC ............ *A61K 33/00* (2013.01); *A61K 9/0053* (2013.01); *A61K 9/167* (2013.01); *A61P 13/12* (2018.01)

(58) Field of Classification Search
CPC ...... A61K 33/00; A61K 9/0053; A61K 9/167; A61P 13/12
See application file for complete search history.

(56) References Cited

U.S. PATENT DOCUMENTS

| | | | |
|---|---|---|---|
| 11,103,527 B2* | 8/2021 | Kobayashi | ............ A61K 33/00 |
| 2005/0079167 A1 | 4/2005 | Sonobe et al. | |
| 2010/0278931 A1 | 11/2010 | Ashton et al. | |
| 2015/0272965 A1 | 10/2015 | Ashton et al. | |
| 2017/0128464 A1 | 5/2017 | Ashton et al. | |
| 2019/0038664 A1 | 2/2019 | Kobayashi et al. | |
| 2019/0216082 A1 | 7/2019 | Kobayashi et al. | |
| 2019/0231660 A1 | 8/2019 | Kobayashi et al. | |

FOREIGN PATENT DOCUMENTS

| | | |
|---|---|---|
| JP | 2010-6843 A | 1/2010 |
| JP | 5514140 B2 | 4/2014 |
| JP | 2015-113331 A | 6/2015 |

(Continued)

OTHER PUBLICATIONS

Kobayashi et al, Renoprotective and Neuroprotective Effects of Enteric Hydrogen Generation for Si-based Agents, Scientific Reports. (Year: 2020).*

(Continued)

*Primary Examiner* — Carlos A Azpuru
(74) *Attorney, Agent, or Firm* — Seed IP Law Group LLP

(57) ABSTRACT

One drug (solid preparation) 100 of the present invention is a drug for a disease of kidney that contains a silicon fine particle, an aggregate of the silicon fine particles, or a crystal grain of silicon having a hydrogen-generating ability. Hydrogen generated from the silicon fine particle in the drug can contribute to the prevention and/or treatment of the kidney disease.

14 Claims, 10 Drawing Sheets

(56) References Cited

FOREIGN PATENT DOCUMENTS

| JP | 2015-143257 | A | | 8/2015 |
|---|---|---|---|---|
| JP | 2016-155118 | A | | 9/2016 |
| JP | 2017-104848 | A | * | 6/2017 |
| WO | 2007/026533 | A1 | | 3/2007 |
| WO | 2017/130709 | A1 | | 8/2017 |
| WO | 2018/037752 | A1 | | 3/2018 |
| WO | 2018/037818 | A1 | | 3/2018 |
| WO | 2018/037819 | A1 | | 3/2018 |

OTHER PUBLICATIONS

Chinese Office Action dated Jun. 7, 2021, for the corresponding Chinese Patent Application No. 201880047302.0, 21 pages. (With English Translation).
Communication pursuant to Article 94(3) EPC dated May 31, 2021, for the corresponding European Patent Application No. 18838677.5, 5 pages.
Japanese Office Action, dated Jun. 14, 2022, for Japanese Application No. 2020-000601 8 pages, with English translation.
European Communication, dated Nov. 23, 2022, for European Application No. 18 838 677.5-1112. (4 pages).
Chinese Office Action, dated Nov. 5, 2021, for Chinese Application No. 201880047302.0 10 pages, with English translation.
"Development of a Technique to Enhance the Immunoactivation Effects of Oligonucleotide Therapeutics with Nanoparticles," National Institute of Materials Science, Jul. 24, 2012, 18 pages. (with English translation).
Extended European Search Report, dated Jun. 23, 2020, For European Application No. 18838677.5-1112, 9 pages.
Imamura et al., "Hydrogen generation from water using Si nanopowder fabricated from swarf," *J Nanopart Res 18*(116), Apr. 2016, 7 pages.
Li et al., "Hydrogen-Rich Saline Promotes the Recovery of Renal Function after Ischemia/Reperfusion Injury in Rats via Anti-apoptosis and Anti-inflammation," *Front. Pharmacol.* 7(106), Apr. 2016, 9 pages.
Matsuda et al., "Concentration of hydrogen molecules and splitting water using silicon nanoparticle," ISIR Osaka University, 4 pages. (with English translation).
Nakayama, "Hydrogen as Reno-protector: Does It Quench Radical Oxygen Species?," Chronic Kidney Disease Dialysis Treatment Joint Research Department, Tohoku University Hospital/Advanced and Integrated Renal Science Core Center, Tohoku University, 13 pages. (with English translation).
Zhu et al., "Intake of water with high levels of dissolved hydrogen ($H_2$) suppresses ischaemia-induced cardio-renal injury in Dahl salt-sensitive rats," *Nephrol Dial Transplant (2011)* Dec. 26, 2010, pp. 2112-2118. (7 pages).
Japanese Office Action, dated Dec. 12, 2023, for Japanese Application No. 2023-001593 8 pages, with English translation. D1-D4 previously cited.

* cited by examiner

100

DRUG AND PRODUCTION METHOD THEREFOR

TECHNICAL FIELD

The present invention relates to a drug, and particularly relates to a drug for kidney disease, and a production method therefor.

BACKGROUND ART

The number of patients suffering from kidney disease, which is also pointed out to be associated with metabolic syndrome (lifestyle-related diseases), is increasing year by year. In Japan, it is said that one of eight adults aged 20 or above has chronic kidney disease. For example, when renal function injury chronically persists to cause exacerbation, harmful substances accumulate in blood, which cause uremia including disturbance of consciousness and the like. It has been pointed out that deterioration in the renal function causes hypertension and hyperphosphatemia to increase the risk of causing serious cardiovascular disturbances such as cerebral infarction and myocardial infarction.

In order to solve the above-mentioned problems, attainment of an organ substitute device or therapeutic agent for removing a toxic substance from the body in place of the kidney, or a preventive medical treatment for preventing the renal function from being deteriorated can be said to be an urgent issue. A typical example of the organ substitute device is an artificial kidney that removes toxic substances during hemodialysis. However, the hemodialysis type artificial kidney is an advanced and special apparatus, so that the hemodialysis type artificial kidney requires a professional engineer and has a great mental and physical burden on the patient. In addition, the increase in the number of patients with kidney disease as described above is easily guessed to cause an enormous medical economic burden for the country employing the universal insurance system.

Meanwhile, with regard to the therapeutic agent for the kidney disease, a technique for employing an oral adsorbent that can be orally taken and can treat disturbance of renal function is disclosed as an alternative to the above-mentioned hemodialysis type artificial kidney (Patent Document 1).

Some of the present inventors have so far advanced researches for preventing hydroxyl radicals from being present in the body. Among superoxide anion radicals as active oxygen, hydroxyl radicals, hydrogen peroxide, and singlet oxygen, the hydroxyl radicals have the strongest oxidizing power without having a physiological function.

Hydrogen is known as an example of substances that eliminate hydroxyl radicals produced in the body. Water is produced by hydrogen reacting with hydroxyl radicals, and water does not produce substances harmful to a living body. Thus, an apparatus for producing hydrogen water containing hydrogen that eliminates hydroxyl radicals in the body has been proposed (for example, Patent Document 2).

However, hydrogen in hydrogen water is easily diffused into air. Thus, for taking hydrogen in the body in an amount necessary for eliminating hydroxyl radicals, it is necessary that the concentration of dissolved hydrogen in hydrogen water is kept high. Therefore, in a method in which hydrogen water is ingested, it is not easy to take hydrogen in the body in an amount sufficient to react the hydrogen with hydroxyl radicals in the body. Thus, in order to easily take hydrogen in the body, a hydrogen-containing composition containing hydrogen and a surfactant has been proposed (Patent Document 3).

Some of the present inventors have studied water decomposition due to silicon nanoparticles, and hydrogen concentrations, and have disclosed the results (Non-Patent Document 1 and Patent Document 4).

PRIOR ART DOCUMENTS

Patent Documents

Patent Document 1: Japanese Patent Laid-Open Publication No. 2010-006843
Patent Document 2: Japanese Patent No. 5514140
Patent Document 3: Japanese Patent Laid-Open Publication No. 2015-113331
Patent Document 4: Japanese Patent Laid-Open Publication No. 2016-155118

Non-Patent Document

Non-Patent Document 1: Shinsuke MATSUDA et al., Water decomposition due to silicon nanoparticles and hydrogen concentrations, Extended Abstracts of the 62nd JSAP Spring Meeting, 2015, 11a-A27-6

SUMMARY OF THE INVENTION

Problems to be Solved by the Invention

When mention is made of the kidney disease, a step of preparing a thermosetting resin, and further oxidizing and reducing spherical activated carbon prepared by using the thermosetting resin as a carbon source is required in order to prepare surface-modified spherical activated carbon even if the oral adsorbent of Patent Document 1 is employed. When the oral adsorbent is orally taken for therapeutic purposes, a considerable amount of internal use thereof is required, which causes an increase in a patient's mental burden. This is easily guessed to cause a decrease in adherence and a decrease in the rate of completion of internal use. Furthermore, when the oral adsorbent is orally ingested together with other drugs, there is a high possibility that the effects of the drugs are likely to be absorbed to the oral adsorbent, which makes it necessary to make the ingestion time of the oral adsorbent different from that of the other drugs. This also promotes the above-mentioned decrease in the rate of completion. Therefore, it can be said to be still halfway to attain the simplification, low cost, high functionality, and/or more accurate safety of the producing step of the therapeutic agent or preventive agent for the kidney disease. A method disclosed in Patent Document 3 makes it very difficult to give hydrogen sufficient to exhibit its function into the body.

As far as the inventors know, efforts to prevent or treat the renal function from the point of view different from an "oral adsorbent" as a drug that can be orally taken are hardly disclosed.

Meanwhile, when mention is made of hydrogen water that has been developed for the purpose of reducing or eliminating excess hydroxyl radicals in the body, hydrogen water is attempted to be employed to take in hydrogen for eliminating the hydroxyl radicals into the body. Even when high-concentration hydrogen water is ingested, the amount of hydrogen contained in 1 liter of hydrogen water is only 18 ml (milliliter) in terms of a gas, even in a saturated state at room temperature. In addition, the saturated water concentration of 1.6 ppm is rapidly decreased in the air, and much of hydrogen in hydrogen water is gasified in an upper digestive tract such as a stomach. This disadvantageously causes pneumophagia (so-called "burp") because a sufficient amount of hydrogen is not necessarily taken in the body. When a hydrogen-containing composition with hydrogen encapsulated by a surfactant is ingested, it is necessary to ingest a large amount of the hydrogen-containing composition for taking a sufficient amount of hydrogen in the body. In addition, there may arise the above-mentioned problem that hydrogen is released in the stomach. Furthermore, even if hydrogen is taken into the body and transported to each organ, the hydrogen concentration in the organ returns to the concentration before the ingestion of hydrogen water after elapse of about 1 hour. Therefore, since the hydroxyl radicals are always produced by respiration and/or metabolism, the effect of ingesting the hydrogen water is limited.

Solutions to the Problems

The present invention solves at least one of the above-mentioned technical problems. The present invention utilizes a silicon fine particle, an aggregate of the silicon fine particle, a crystal grain of silicon (particle diameter of about 1 μm to about 2 μm) or a silicon grain having a surface area equivalent to that of the silicon fine particle (preferably porous particles having nano-order voids), having a hydrogen-generating ability to largely contribute to the attainment of the prevention or treatment of renal disease different from means or approaches employed so far.

The present inventors found that, even if the above-mentioned silicon fine particle or aggregate thereof, or crystal grain of silicon are brought into contact with a water-containing liquid having a very low pH value (that is, strongly acidic) such as stomach acid, the silicon fine particle or aggregate thereof, or the crystal grain of silicon hardly generate hydrogen, but the silicon fine particle or aggregate thereof, or the crystal grain of silicon can significantly generate hydrogen when being brought into contact with a portion or a water-containing liquid that has a pH value in a neutral numerical range (including a pH value of 6 to 7 in the present application) to an alkaline numerical range. Based on these facts, the present inventors repeatedly conducted various experiments and analyzes in order to investigate the possibility that the above-mentioned silicon fine particle or aggregate thereof, or crystal grain of silicon contribute to the prevention or treatment of the kidney disease. As a result, significant effects on the kidney disease could be confirmed.

At present, the present inventors consider that reduction in hydroxyl radicals in the body due to hydrogen produced from the above-mentioned silicon fine particle or aggregate thereof or crystal grain of silicon contributes to the prevention and/or treatment of the kidney disease. The "water-containing liquid" in the present application includes water itself and human body fluid.

Here, a hydrogen generation mechanism by the reaction of the silicon fine particle or the crystal grain of silicon with water molecules is represented by the following formula (Chemical Formula 1). However, as described above, the present inventors found that the reaction represented by the formula (chemical formula 1) is a limited reaction when the silicon fine particle or the crystal grain of silicon are brought into contact with a water-containing liquid having a low pH value (typically a pH value of less than 5), but the reaction proceeds when the silicon fine particle or the crystal grain of silicon are brought into contact with a water-containing liquid having a pH value of 6 or more (particularly, more than 6). Therefore, it was very interestingly clarified that even a water-containing liquid that is weakly acidic and has a pH value of 6 allows effective generation of hydrogen. The present inventors found by further examination that, in order to promote the generation of hydrogen, it is effective to bring the silicon fine particle or the crystal grain of silicon into contact with more suitably a water-containing liquid having a pH value of 7 or more (or more than 7), still more suitably a water-containing liquid having a pH value of more than 7.4, and very suitably a water-containing liquid that is basic (hereinafter referred to as "alkaline") and has a pH value of more than 8. In the present application, a basic water-containing liquid in a basic or biocompatible range of an intestinal fluid determines the upper limit of the pH value.

   (Chemical Formula 1)

Based on the above-mentioned findings, the present inventors found that at least a part of the above-mentioned technical problems can be solved by utilizing the above-mentioned silicon fine particle or aggregate thereof, or crystal grain of silicon for kidney disease. The present invention has been made based on the above-mentioned viewpoint.

One drug of the present invention is a drug for a disease of kidney containing a silicon fine particle, an aggregate of the silicon fine particles or a crystal grain of silicon having a hydrogen-generating ability.

In the drug, hydrogen generated from the above-mentioned physiologically acceptable silicon fine particle or aggregate of the silicon fine particles (hereinafter, also collectively referred to as "silicon fine particle"), crystal grain of silicon (particle size of about 1 μm to about 2 μm), or a silicon particle of 1 μm or more having a surface area equivalent to that of the silicon fine particle is considered to contribute to reduction in hydroxyl radicals in the body. At present, the detailed mechanism is not clear, but such reduction in hydroxyl radicals is considered to be able to contribute to the prevention and/or treatment of the kidney disease. The specific effect of the prevention, treatment, or improvement of the kidney disease has been confirmed by the drug.

Even when the above-mentioned drug is brought into contact with a water-containing liquid having a very low pH value such as stomach acid, the drug hardly generates hydrogen. However, when the drug is brought into contact with a portion or a water-containing liquid that has a pH value in neutral to alkaline numerical ranges, the ability to significantly generate hydrogen can significantly contribute to the prevention, treatment, or improvement of the kidney disease.

A production method for a substance of a drug of the present invention is a production method for a substance of the above-mentioned drug, the method including a step of forming the above-mentioned silicon fine particle and/or aggregate of the silicon fine particles, or crystal grain of silicon by grinding a silicon particle in an ethanol solution, and a hydrogen peroxide water treatment step of bringing the silicon fine particle, and/or the aggregate, or the crystal grain of silicon into contact with hydrogen peroxide water.

The production method for a substance of a drug can produce the drug that can contribute to reduction in hydroxyl radicals in the body due to hydrogen generated from the above-mentioned physiologically acceptable silicon fine particle or crystal grain of silicon (particle size of about 1 μm to about 2 μm). At present, the detailed mechanism is not clear, but such reduction in hydroxyl radicals is considered to be able to contribute to the prevention and/or treatment of the kidney disease.

In the actual use of the above-mentioned drug, the use of at least one kind selected from the group of fine particles of 100 nm or more (or more than 100 nm) that have a surface area equivalent to that of the silicon fine particle, and are porous, polycrystalline, or unfree, hardly crushed or granulated with an undecomposed binding agent, and porous crystal grains can also be employed as an aspect.

In the present application, the expression "crystallite" is employed rather than the expression "crystal grain (or crystal particle)" when the diameter of a crystal is in the "nm order." Meanwhile, the expression "crystal grain (or crystal particle)" is employed when the diameter of a crystal is in the "μm order." In the present application, the expression "grain" is employed as the expression regardless of the presence or absence of crystallinity.

Here, the "silicon fine particle" in the present application includes a "silicon nanoparticle" having an average crystallite diameter in the nm order, specifically a crystallite diameter of substantially 1 nm or more and 100 nm or less. In a narrower sense, the "silicon fine particle" in the present application includes, as main particles, a silicon nanoparticle having an average crystallite diameter at a nano level, specifically a crystallite diameter of 1 nm or more and 50 nm or less. Here, according to the present inventors, a silicon nanoparticle having a main crystallite diameter of 1 nm or more and less than IO nm is the "silicon fine particle" that attains the finest division as one employable aspect. In the present application, the silicon fine particle includes not only individually dispersed silicon nanoparticles, but also silicon nanoparticles in a state of an aggregate that is formed by natural gathering of a plurality of the silicon nanoparticles and has a size close to a μm size (generally 0.1 μm or more), fused silicon nanoparticles, and granulated silicon nanoparticles that cause no redispersion. The "silicon fine particle" in the present application may include porous silicon.

As described above, the "silicon fine particle" in the present application can be aggregated in a natural state to form an aggregate having a diameter size at a μm level (for example, about I μm). In the present application, a lump solid preparation that is obtained by artificially putting the silicon fine particles together through addition of a binding agent, compression, or the like and has such a size to be picked up by human fingers is sometimes referred to as "solid preparation" for discriminating the solid preparation from the "aggregate" and the "crystal grain." The "drug" in the present application includes a "solid preparation". Typical examples of the "solid preparation" include tablets, and granules or a powdered drug that assume a powdery form rather than a lump form.

In the present application, the expression "disease" includes "malady", "disease", and "injury" meanings. The "physiologically acceptable base material (substance or material)" in the present application is a base material (substance or material) that is substantially innocuous and causes substantially no side effect or harmful reaction even when brought into contact with the skin or the mucous membrane. The term "physiologically" includes a "medical" meaning.

Effects of the Invention

In one drug of the present invention, hydrogen generated from the above-mentioned physiologically acceptable silicon fine particle can contribute to the prevention and/or treatment of kidney disease.

A production method for a substance of the drug of the present invention can produce the drug that can contribute to reduction in hydroxyl radicals in the body due to hydrogen generated from the above-mentioned physiologically acceptable silicon fine particle. As a result, a drug that can contribute to the prevention and/or treatment of current renal disease can be produced.

BRIEF DESCRIPTION OF THE DRAWINGS

FIG. 9A shows a kidney of a rat ingesting a normal diet, and FIG. 9B shows a kidney of a rat ingesting a feed that contains a normal diet and silicon particles added to the normal diet.

DESCRIPTION OF REFERENCE SIGNS

100: Solid preparation

EMBODIMENTS OF THE INVENTION

Figure 1A:
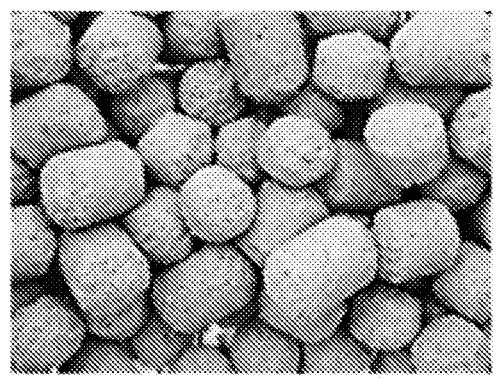
FIG. 1A shows a photograph of a normal feed and FIG. 1B shows a photograph of a solid preparation (feed) of a first embodiment.

Embodiments of the present invention will be described in detail with reference to the accompanying drawings.

First Embodiment

A solid preparation of the present embodiment contains a silicon fine particle or an aggregate of the silicon fine particles (hereinafter, also collectively referred to as "silicon fine particle") or a crystal grain of silicon having a hydrogen-generating ability. Hereinafter, the silicon fine particle, and the solid preparation containing the silicon fine particle or the crystal grain as an example of a "drug" of the present embodiment will be described in detail. In addition, a production method for a drug of the present embodiment, or a production method for a substance of the drug will also be described in detail.

[1] Silicon Fine Particle (or Crystal Grain of Silicon), Solid Preparation, and Production Method Therefor The solid preparation according to the present embodiment is produced using a silicon fine particle (hereinafter, also typically referred to as "silicon nanoparticle") that may contain a silicon nanoparticle obtained by finely dividing, according to a bead mill method, a commercially available high-purity silicon particle powder (typically, manufactured by Kojundo Chemical Laboratory Co., Ltd., particle diameter distribution: <φ 5 μm (but silicon particles having a crystal grain diameter of more than 1 μm, purity: 99.9% i-type silicon) as a silicon particle. The present embodiment employs a step of forming the silicon fine particle or the aggregate of the silicon fine particles by grinding a silicon particle in an ethanol solution. The method disclosed in the present embodiment is not limited to the above-described method.

Specifically, 200 g of the high-purity silicon powder is dispersed in 4 L (litters) of a 99.5 wt % ethanol solution using a bead mill apparatus (manufactured by AIMEX CO., Ltd. horizontal continuous ready mill, (model: RHM-08), and φ 0.5 μm zirconia beads (volume: 750 ml) are added thereto. The mixture is finely divided by performing grinding (one-step grinding) at a rotation speed of 2500 rpm for 4 hours. In the present embodiment, grinding in which the size and/or type of the beads are/is appropriately changed may be employed for the purpose of adjusting a required particle size or particle size distribution or the like. Therefore, the apparatus and method disclosed in the present embodiment are not limited.

In the present embodiment, a separation slit provided in a grinding chamber of the bead mill apparatus separates the mixture into the beads and an ethanol solution containing silicon fine particles. The ethanol solution containing silicon fine particles that has been separated from the beads is heated to 30° C. to 35° C. with a vacuum evaporator. As a result, the ethanol solution is evaporated to provide the silicon fine particle and/or aggregate thereof.

The silicon fine particle obtained by the method and capable of serving as a substance of a drug of the present embodiment mainly contain a silicon fine particle having a crystallite diameter of 1 nm or more and 100 nm or less. More specifically, as a result of measuring the silicon fine particle by an X-ray diffractometer (SmartLab manufactured by Rigaku Corporation), the following values were obtained as one example. In a volume distribution, the mode diameter was 6.6 nm; the median diameter was 14.0 nm; and the average crystallite diameter was 20.3 nm.

The silicon fine particle was observed using a scanning electron microscope (SEM), and the result showed that the silicon fine particles were partially aggregated to form a slightly large formless aggregate of about 0.5 μm or less. Individual silicon fine particles were observed using a transmission electrode microscope (TEM), and the result showed that main silicon fine particles had a crystallite diameter of about 2 nm or more and nm or less.

Thereafter, a first mixing step of mixing hydrogen peroxide water with the silicon fine particles in a glass container (hereinafter, also referred to as a "H2O2 treatment" or a "hydrogen peroxide water treatment step") is performed in the present embodiment. In the present embodiment, the temperature of the hydrogen peroxide water (3.5 wt % in the present embodiment) in the mixing step is 75° C. The mixing time is 30 minutes. A sufficient stirring treatment in the first mixing step (hydrogen peroxide water treatment step) is preferred to increase the opportunity of the silicon fine particles being brought in contact with the hydrogen peroxide water. Even when the temperature of the hydrogen peroxide water in the first mixing step (hydrogen peroxide water treatment step) is, for example, about room temperature, at least a part of the effects of the present embodiment can be exhibited. The silicon fine particles that have been subjected to the first mixing step can also serve as the substance of the drug of the present embodiment.

The silicon fine particles mixed with the hydrogen peroxide water are subjected to a solid-liquid separation treatment using a known centrifugal separator to remove the hydrogen peroxide water and thus provide silicon fine particles. As a result, it is possible to obtain silicon fine particles having surfaces treated with hydrogen peroxide water. Here, the treatment of the surfaces of the silicon fine particles with hydrogen peroxide water can remove an alkyl group (for example, a methyl group) present on the surfaces of the silicon fine particles. As a result, the silicon fine particles and aggregates thereof can form a state where they have surfaces capable of being brought into direct contact with a medium capable of containing a water-containing liquid, while as a whole retaining hydrophilicity on their surfaces. Such a special surface treatment can promote the generation of hydrogen with higher accuracy.

Thereafter, a second mixing step of mixing the silicon fine particles with an ethanol solution is further performed in the present embodiment. A sufficient stirring treatment in the mixing step is preferred to increase the opportunity of the silicon fine particles being brought into contact with the ethanol solution (99.5 wt % in the present embodiment). The silicon fine particles mixed with the ethanol solution are subjected to a solid-liquid separation treatment using a known centrifugal separator for removing the ethanol solution that is highly volatile, followed by sufficiently drying to produce silicon fine particles as one example of the present embodiment. The silicon fine particles that have been subjected to the second mixing step can also serve as the substance of the drug of the present embodiment.

In the present embodiment, as another type of final silicon fine particles, silicon fine particles were also produced, with the mixing time of the hydrogen peroxide water with the silicon fine particles set to 60 minutes in the first mixing step of the above-mentioned steps. By adjusting the treatment time of the bead mill method, and the like, in place of the silicon fine particle, a crystal grain of silicon (for example, a crystal grain of silicon that substantially contains no "silicon nanoparticles" of 1 nm or more and 100 nm or less) can also be produced through at least the above-mentioned first mixing step. The above-mentioned crystal grains of silicon can also serve as the substance of the drug of the present embodiment.

In the present embodiment, isopropyl alcohol or hydrofluoric acid (aqueous solution) is not used. The present embodiment uses the ethanol solution and the hydrogen peroxide water in order to obtain the silicon fine particles (or the aggregates thereof) or the crystal grains of silicon, and thus, it is worth noting that it is possible to provide a drug (or a solid preparation) that is safer and more secure for a living body, a production method for the drug (or the solid preparation), or a production method for a substance of the drug (or the solid preparation).

Figure 1B:

The present embodiment further produce the solid preparation containing the silicon fine particles (including the aggregates thereof) and/or the crystal grains of silicon that can serve as the substance of the drug of the present embodiment. The solid preparation of the present embodiment is an experimental sample (or feed) described later. FIG. 1A is an overview photograph of a normal feed as Comparative Example, and FIG. 1B is an overview photograph of a normal feed in which silicon fine particles according to the present embodiment are kneaded.

In the present embodiment, thereafter, a pH value adjusting agent adding step is performed, in which 97.5 wt % of a normal feed (manufactured by Oriental Yeast Co., Ltd., model number: AIN93M) as a base material, and 2.5 wt % of the above-mentioned produced silicon fine particles (and/or crystal grains of silicon) are kneaded using a known kneader together with an aqueous solution of citric acid as a pH value adjusting agent. The amount of the aqueous solution of citric acid is not particularly limited, but for example, about 0.5 wt % of the aqueous solution with respect to the total amount of the silicon fine particles (and/or the crystal grains of silicon) and the feed can be selected. The pH value of the aqueous solution of citric acid is about 4. The type of the base material is not limited as long as it is a physiologically acceptable base material (substance or material).

Thereafter, the feed obtained by kneading the silicon fine particles (and/or crystal grains of silicon) is molded using a commercially available pelleter. Thereafter, moisture is removed using a dryer heated to about 90° C., and the size of the molded product is selected using a sieve, whereby a solid preparation (feed) 100 shown in FIG. 1(b) can be produced. Thereafter, from the viewpoint of preventing or inhibiting the solid preparation (feed) 100 from being brought into contact with moisture, one suitable aspect is storing the solid preparation (feed) 100 in a packaged state. An aspect in which the silicon fine particles (including the aggregates thereof) that do not form the solid preparation 100 are contained in a known material (base material) other than the normal feed is also one employable aspect.

Here, citric acid contained in the solid preparation 100 of the present embodiment can serve as a pH value adjusting agent that sets the pH value of the water-containing liquid when the solid preparation 100 is disintegrated in pure water to 4 or more and less than 7 (more narrowly, 6 or less). As a result, the adjustment action of the pH value by citric acid that sets the water-containing liquid to an acidic state can prevent or inhibit the generation of hydrogen due to the solid preparation 100 being brought into contact with moisture and the like in the outside air. Therefore, as one suitable aspect of the present embodiment, the solid preparation 100 contains the citric acid. Even when the solid preparation of the present embodiment does not contain the citric acid, at least a part of the effects of the present embodiment can be exhibited.

Modified Example (1) of First Embodiment

In the production method for the drug (or solid preparation 100) of the first embodiment, or the production method for the substance of the drug (or solid preparation 100), one suitable aspect is further including an introduction step of introducing a "pH adjusting agent" into the drug (or solid preparation). The pH adjusting agent makes adjustment so as to satisfy a condition where hydrogen is more likely to be generated in an appropriate environment in the body, in other words, so as to set a pH value in a numerical value in which hydrogen is more likely to be generated.

The citric acid in the first embodiment is one example of the "pH adjusting agent," but the "pH adjusting agent" is not limited to the citric acid. The material for the "pH adjusting agent" is not limited as long as it is a material (hereinafter, also referred to as an acid agent) allowing adjustment to acidity having a pH value of 2 or more (more preferably 3 or more) and less than 7 (more preferably 6 or less). A typical example of the acid agent is at least one selected from the group consisting of citric acid, gluconic acid, phthalic acid, fumaric acid, and lactic acid, or a salt thereof. One suitable aspect is employing a material widely used as a food additive and having advantages such as excellent safety and versatility.

Modified Example (2) of First Embodiment

One suitable aspect is preparing the drug (or solid preparation 100) of the first embodiment so as to be suitable for oral ingestion in order to improve the taking property of the silicon fine particles or crystal grains of silicon of the first embodiment. For example, another suitable aspect is employing a known jelly preparation of the solid preparation 100, or employing known preparations such as a microgranule agent, a liquid agent, a dry syrup agent, a chewable agent, a troche agent, and a fine granule agent and the like.

It is preferable to prepare each of the above-mentioned preparations so as to have a sustained release property because hydrogen is more likely to be generated in an appropriate environment in the body (for example, in an intestinal tract that is downstream from a stomach). Specifically, as one suitable aspect, the solid preparation 100 has a sustained release property for generating hydrogen in the intestinal tract (for example, in the whole intestinal tract) to exhibit a pharmacological function. Examples of other means for exhibiting a sustained release property include adjustment of the particle size distribution of silicon fine particles, adjustment of a coating material, and/or storage of the solid preparation in a capsule (including a microcapsule) that can function as a sustained-release agent described later. The form of the preparation is not also particularly limited, and the preparation can be employed in a wide form. Therefore, the dosage form and form of the drug (or solid preparation 100) for kidney disease of the present embodiment are not limited to the above-mentioned dosage forms and forms.

Modified Example (3) of First Embodiment

In the present embodiment, the same high-purity silicon particle powder as that used in the first embodiment (typically, silicon particles having a crystal grain diameter of more than 1 μm) is ground in one step by the procedures described in the first embodiment. In the present embodiment, the φ 0.5 μm zirconia beads (volume: 750 ml) used in the one-step grinding are automatically separated from a solution containing silicon fine particles in a bead mill grinding chamber. Furthermore, φ 0.3 μm zirconia beads (volume: 300 ml) are added to the solution containing silicon fine particles from which the beads have been separated, and the mixture is finely divided by performing grinding (two-step grinding) at a rotation speed of 2500 rpm for 4 hours.

The silicon fine particles containing the beads are separated from the solution containing silicon fine particles as described above. The ethanol solution containing silicon fine particles that has been separated from the beads is heated to 40° C. using a vacuum evaporator in the same manner as in the first embodiment, whereby the ethanol solution is evaporated to obtain the silicon fine particles.

Modified Example (4) of First Embodiment

Another employable aspect is also further providing a physiologically acceptable covering layer that covers the solid preparation 100 according to the first embodiment or the solid preparations described in the Modified Examples (1) and (2) of the first embodiment. For example, it is possible to employ a known enteric material hardly soluble in the stomach as a coating agent that covers the outermost layer of the solid preparation 100. An example of a physiologically acceptable covering layer applicable as a capsule preparation is a capsule that encapsulates the silicon fine particle (mainly the aggregate of the silicon fine particles) or the crystal grain of silicon and is produced from a known enteric material hardly soluble in the stomach. When the solid preparation 100 is employed, a disintegrating agent may be further contained. For the disintegrating agent, a known material can be employed. In addition, an example of a more suitable disintegrating agent is an organic acid, and the most suitable example is citric acid. Here, the organic acid can also function as a binding agent that brings the silicon fine particles into a lump form.

In addition, the temperature condition of the water-containing liquid for generating hydrogen in each of the above-mentioned embodiments is not limited. The water-containing liquid capable of generating hydrogen and having a temperature of suitably 30° C. (more suitably 35° C.) or higher and 45° C. or lower promotes the reaction of generating hydrogen.

EXAMPLES

Hereinafter, the above-mentioned embodiments will be described in more detail by way of Examples, but the embodiments are not limited to these examples.

Example 1

The present inventors examined the state of generation of hydrogen without performing a molding step using a pelleter, to evaluate silicon fine particles themselves. Specifically, an experiment was conducted as Example 1, using silicon fine particles subjected to the one-step grinding in the first embodiment.

The silicon fine particles described in the first embodiment in an amount of 10 mg and in a form of a powdered drug (that is, citric acid was not mixed or kneaded) were poured into a glass bottle having a volume of 100 ml (borosilicate glass having a thickness of about 1 mm, LABORAN Screw Tubular Bottle manufactured by AS ONE Corporation). Tap water having a pH value of 7.1 in an amount of 30 ml was poured into the glass bottle. The glass bottle was hermetically sealed under the temperature condition of a liquid temperature of 25° C. The concentration of hydrogen in the liquid in the glass bottle was measured. The hydrogen generation amount was determined using the measured concentration of hydrogen. For measurement of the concentration of hydrogen, a portable dissolved hydrogen meter (Model: DH-35A manufactured by DKK-TOA CORPORATION) was used.

Example 2

Example 2 was conducted in the same manner as Example 1 except that 30 ml of tap water was poured and the temperature condition was changed to a liquid temperature of 37° c.

Figure 4:
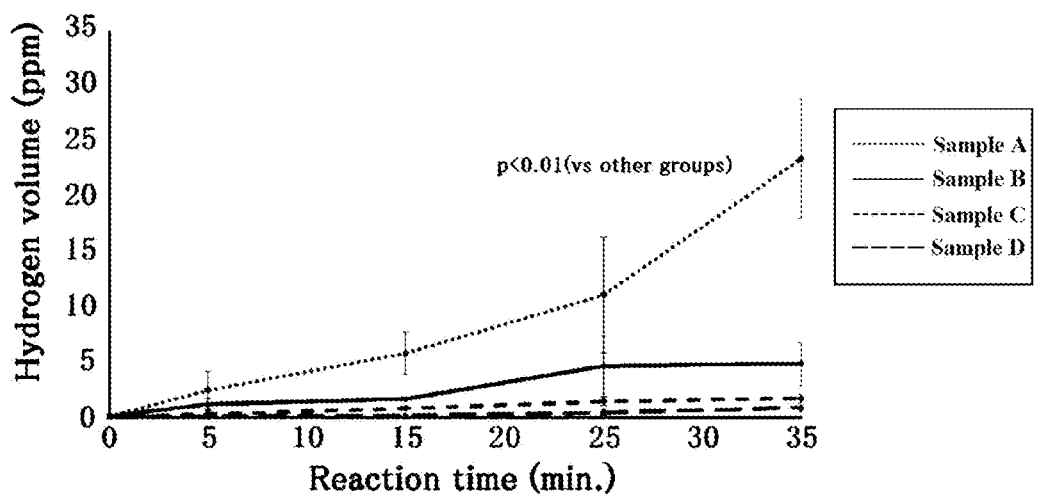
FIG. 4 is a graph showing the relationship between a hydrogen generation amount (ppm) and a reaction time (minute) of each of samples A to D of the first embodiment.

FIG. 4 shows the results of Examples 1 and 2. In FIG. 4, the abscissa axis represents the time (min) during which the solid preparation is kept in contact with the water-containing liquid, and the ordinate axis of the graph represents the hydrogen generation amount.

Figure 2:
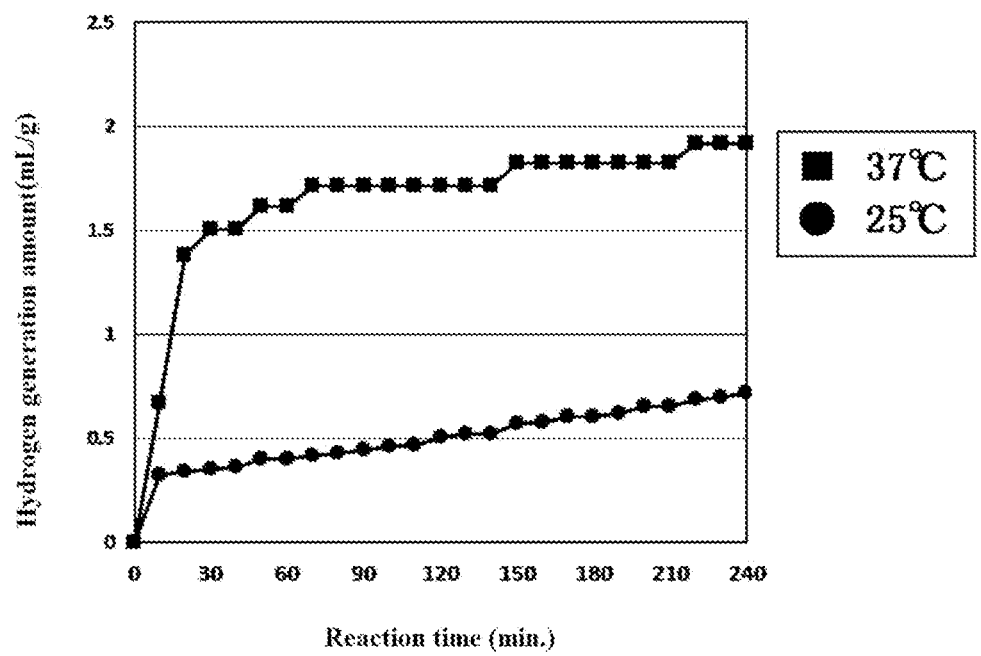
FIG. 2 is a graph showing amounts of hydrogen generated in Examples I and 2.

As shown in FIG. 2, the generation of hydrogen was confirmed even when nearly neutral water was brought into contact with the silicon fine particles described in the first embodiment. It was also clarified that a high liquid temperature increases the hydrogen generation amount. Particularly, it was confirmed that, when the liquid temperature is 37° C. close to human body temperature, the generation of hydrogen is attained in a shorter time and a great amount (1.5 ml/g or more) of hydrogen is continuously generated thereafter.

According to further studies provided by the present inventors, it was clarified that the silicon fine particles or the crystal grains of silicon have a hydrogen generating ability of 5 ml/g or more when they are brought into contact with a water-containing liquid having a pH value of 6 or more and less than 7, and have a hydrogen generating ability of 10 ml/g or more when they are brought into contact with a water-containing liquid having a pH value of more than 7 and less than 9. It was also clarified that the silicon fine particles or the crystal grains of silicon have a hydrogen generating ability of 2 ml/g or less when they are brought into contact with a water-containing liquid having a pH value of I or more and 3 or less. This means that the silicon fine particles or the crystal grains of silicon have almost no hydrogen generating ability, for example, in a human stomach (stomach acid), and exhibit a hydrogen generating ability in contact with, for example, a water-containing liquid in an intestine (typically, intestinal fluid) that is downstream from the stomach, whereby the generation of hydrogen at an appropriate place in the human body can be attained.

<Experiment of Measuring Amount of Hydrogen Generated by Contact Between Silicon Fine Particles and Water-Containing Liquid>

The present inventors also examined the time change of an amount of hydrogen generated by bringing the same silicon fine particles as the silicon fine particles (not the solid preparation) of the first embodiment except that citric acid is not contained into contact with an aqueous solution obtained by dissolving sodium hydrogen carbonate in pure water.

Specifically, 11 mg of the silicon fine particles (first mixing step: 30 minutes) or 5 mg of the silicon fine particles (first mixing step: 60 minutes) are mixed in a glass container with an aqueous solution having sodium hydrogen carbonate (1.88 wt %) dissolved therein. The aqueous solution has a pH of about 8.3. Thereafter, the glass container was filled to its opening with the aqueous solution and covered with a lid so as not to allow entry of air for complete hermetic sealing.

The lid is made of polypropylene, but a multilayer filter of polyethylene and polypropylene was used as an inner lid, whereby transmission and leakage of generated hydrogen can be sufficiently inhibited. Some time later after the hermetic sealing, the silicon fine particles prepared of the present embodiment are visually confirmed to be evenly mixed in the whole aqueous solution from their appearance.

Figure 3A:
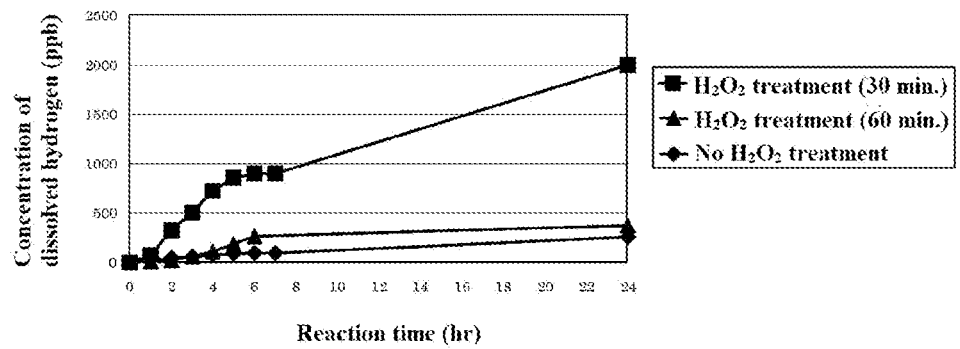
FIG. 3A is a graph showing the time change of an amount of dissolved hydrogen generated by bringing each type of silicon fine particles of the first embodiment subjected into contact with an aqueous solution obtained by dissolving sodium hydrogen carbonate in pure water.
Figure 3B:
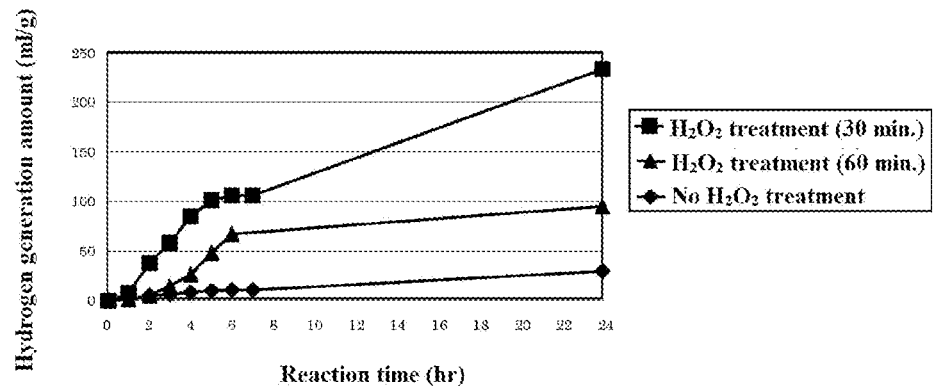
FIG. 3B is a graph showing the time change of an amount of dissolved hydrogen per gram of the silicon fine particles of the first embodiment.

FIG. 3A is a graph showing the time change of a concentration of dissolved hydrogen generated by bringing each type of the silicon fine particles (not the solid preparation) of the first embodiment into contact with an aqueous solution (pH value=8.3) obtained by dissolving sodium hydrogencarbonate in pure water. FIG. 3B is a graph showing the time change of a hydrogen generation amount per gram of each type of the silicon fine particles. For reference, the graphs show the results of using the silicon fine particles not subjected to the first mixing step. The amounts of dissolved hydrogen were measured using a portable dissolved hydrogen meter (manufactured by DKK-TOA CORPORATION, model: DH-35A).

As shown in FIGS. 3A and 3B, it was clarified that the first mixing step promotes the generation of hydrogen. Particularly, as shown in FIG. 3B, it is worth noting that the first mixing step is performed to continuously provide a hydrogen generation amount of 40 ml or more in 2 hours after elapse of 2 hours from the start of generation of hydrogen.

The hydrogen generation amount of the silicon fine particles subjected to the first mixing step with a mixing time of 60 minutes is considered to be smaller than the hydrogen generation amount of the silicon fine particles with a mixing time of 30 minutes due to the difference in thickness of an oxide film on the surfaces of the silicon fine particles. That is, it is considered that the silicon fine particles subjected to the first mixing step with a mixing time of 60 minutes has a thicker oxide film, which makes it difficult to bring the silicon fine particles into direct contact with the medium (aqueous solution) to inhibit the generation of hydrogen.

According to further research and analyses by the present inventors, the silicon fine particles can attain sufficient surface areas capable of being brought into direct contact with the medium, while appropriately retaining hydrophilicity of the surfaces thereof, when subjected to the first mixing step with a mixing time of more than 2 minutes and 50 minutes or less (more suitably 3 minutes or more and 40 minutes or less, more suitably 4 minutes or more and 30 minutes or less, most suitably 5 minutes or more and 20 minutes or less). As a result, the generation of hydrogen can be more accurately promoted with the mixing time fallen within the above-mentioned range.

<Experiment of Measuring Amount of Hydrogen Generated by Contact Between Solid Preparation and Water-Containing Liquid>

In addition to the above-mentioned results of Examples I and 2, the present inventors evaluated the hydrogen generation amounts (ppm) related to the following four samples A to D under different conditions for the solid preparation 100 of the first embodiment subjected to molding by a pelleter.

Example 3

A sample A is obtained by charging 200 mg of a ground product obtained by grinding a solid preparation once molded by a pelleter into 2 ml of a water-containing liquid having a pH value of 8.2. (water-containing liquid: pure water)

A sample B is obtained by charging 200 mg of a solid preparation into 2 ml of a water-containing solution having a pH value of 8.2. (water-containing liquid: pure water)

A sample C is obtained by charging 200 mg of a ground product obtained by grinding a solid preparation once molded by a pelleter into 2 ml of pure water.

A sample D is obtained by charging 200 mg of a solid preparation into 2 ml of pure water.

FIG. 4 is a graph showing the relationship between a hydrogen generation amount (ppm) and a reaction time (minutes) of each of the above-mentioned samples A to D. As shown in FIG. 4, it was confirmed that the ground product of the solid preparation tends to have a significantly more hydrogen generation amount with the passage of time than that of the unground solid preparation. This suggests that, for example, the hydrogen generation amount when the solid preparation bitten by the human enters the body is greater than that when the human swallows the solid preparation as it is. The water-containing liquid having a pH value of 8.2 tended to generate more hydrogen than that of pure water, which suggested that the reaction with the intestinal fluid provides an increase in the hydrogen generation amount.

<Effect Confirmation Experiment when Causing SD Rat Aged 6 Weeks to Ingest Normal Feed or Solid Preparation (Feed) for 8 Weeks>

Figure 5:
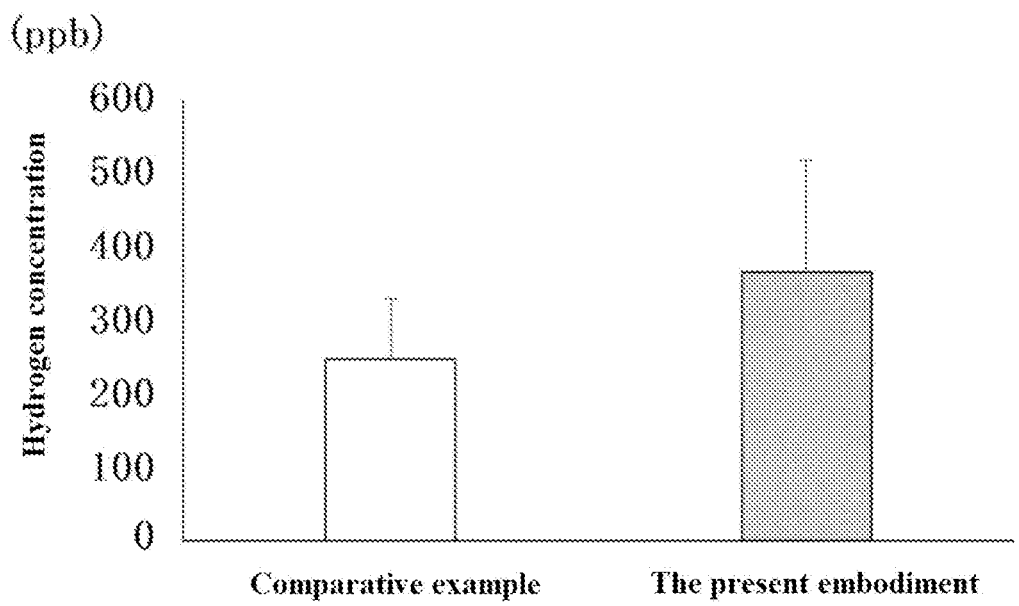
FIG. 5 is a graph showing a hydrogen concentration (ppb) in 200 μl (microliter) of blood when an SD rat aged 6 weeks is caused to ingest a normal feed or a solid preparation (feed) of the first embodiment for 8 weeks.
Figure 6:
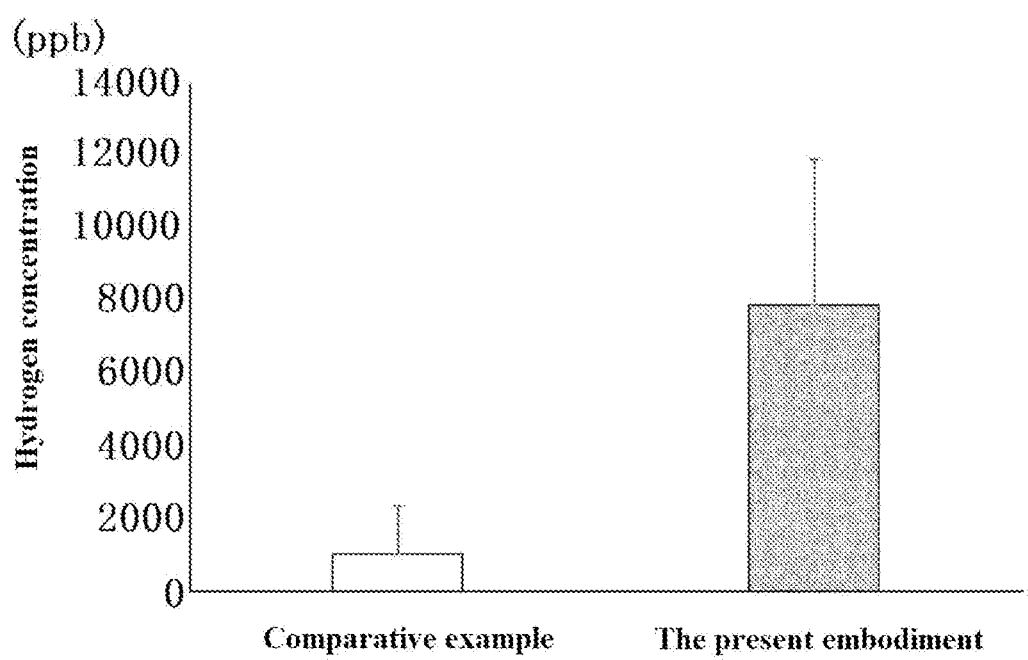
FIG. 6 is a graph showing a hydrogen concentration (ppb) in exhaled air when an SD rat aged 6 weeks is caused to ingest a normal feed or a solid preparation (feed) of the first embodiment for 8 weeks.

FIG. 5 is a graph showing a hydrogen concentration (ppb) in 200 μl (microliter) of blood when an SD rat aged 6 weeks (Sprague-Dawley rat, referred to as an "SD rat" in the present application) is caused to ingest a normal feed (Comparative Example in FIG. 5) or a solid preparation (feed) (the present embodiment in FIG. 5) for 8 weeks. In addition, FIG. 6 is a graph showing a hydrogen concentration (ppb) in exhaled air when an SD rat aged 6 weeks is caused to ingest a normal feed (Comparative Example in FIG. 6) or a solid preparation (feed) (the present embodiment in FIG. 6) for 8 weeks. The hydrogen concentration in the blood was measured with a sensor gas chromatograph apparatus (model: SGHA-P2 manufactured by FIS, Inc.). The hydrogen concentration in the exhaled air was similarly measured with a sensor gas chromatograph apparatus (model: SGHA-P2 manufactured by FIS, Inc.) after leaving the rat in a completely sealed container for 8 minutes.

As shown in FIGS. 5 and 6, the rat (the present embodiment) ingesting the solid preparation (feed) was confirmed to have a higher hydrogen concentration in the blood and the exhaled air. The difference in the hydrogen concentration in the blood is considered to be relatively small because the hydrogen generated from the solid preparation is rapidly diffused outside the body. Hydroxyl radicals may be involved in exacerbation of disturbance of renal function.

Therefore, from the results of FIGS. 5 and 6, the increase in the hydrogen concentration in the blood and/or the exhaled air suggests that the hydrogen generated from the solid preparation of the present embodiment may contribute to the effect of inhibiting deterioration in the above-mentioned renal function or retaining the renal function (typically, the effect of inhibiting the progression of chronic renal failure) or the effect of improving the renal function.

Figure 7:
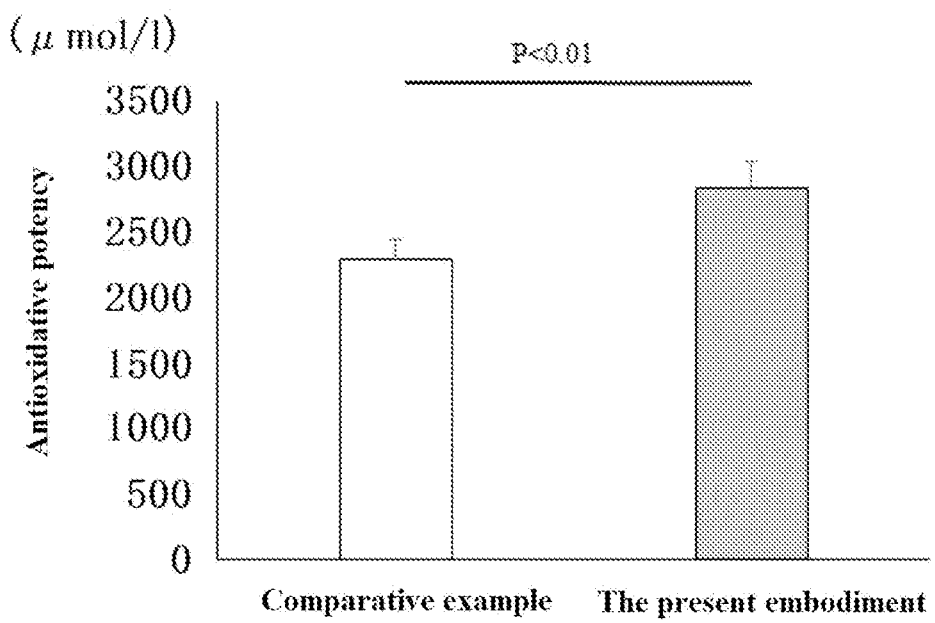
FIG. 7 is a graph showing the results of a BAP test (evaluation test of antioxidative potency of blood plasma) for measuring an antioxidation degree when an SD rat aged 6 weeks is caused to ingest a normal feed or a solid preparation (feed) of the first embodiment for 8 weeks.

FIG. 7 is a graph showing the result of a BAP test (evaluation test of antioxidative potency of blood plasma) for measuring an antioxidation degree when an SD rat aged 6 weeks is caused to ingest a normal feed (Comparative Example in FIG. 7) or a solid preparation (feed) (the present embodiment in FIG. 7) for 8 weeks. The BAP test was measured with a FREE Carrio Duo apparatus (manufactured by Diacron International, model: DI-601M).

As shown in FIG. 7, the rat (the present embodiment) ingesting the solid preparation (feed) was confirmed to have significantly higher antioxidative potency. Therefore, it was clarified that the administration of the solid preparation of the present embodiment exhibits the effect of inhibiting the deterioration in the renal function or maintaining the renal function (typically, the effect of inhibiting the progression of chronic renal failure), or the effect of improving the renal function.

<Confirmation Experiment of Preventive Effect Due to Solid Preparation of First Embodiment Using 5/6 Nephrectomized Rat Model>

Figure 8:
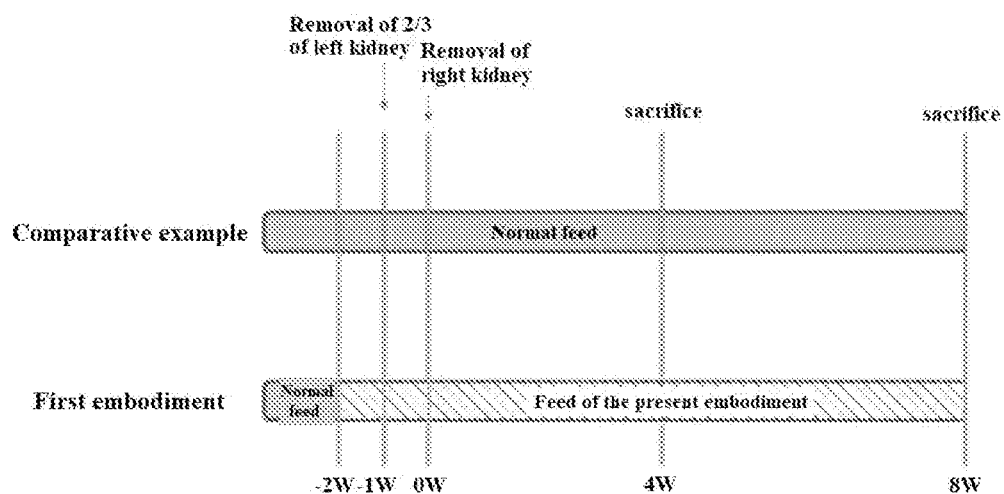
FIG. 8 is an execution plan (protocol) for confirming the preventive effect of a solid preparation of the first embodiment using a 5/6 nephrectomized rat model.

Based on each of the above-mentioned basic experiments, the present inventors conducted a confirmation experiment for a preventive effect due to a solid preparation 100 of the first embodiment using a 5/6 nephrectomized rat model. FIG. 8 is an execution plan (protocol) for confirming the preventive effect of a solid preparation 100 of the first embodiment using a 5/6 nephrectomized rat model. In each of FIGS. 8 to 18, "W" represents the number of weeks from the start of observation of the 5/6 nephrectomized rat model. For example, "4W" means 4 weeks from the start of observation of the 5/6 nephrectomized rat model.

Example 4

In the present experiment, the following two types of 5/6 nephrectomized rat models ((1) Comparative Example and (2) first embodiment (hereinafter, also referred to as "the present embodiment" until leading to the description of a second embodiment)) were used for comparison.

(1) Comparative Example (control group): only a normal feed shown in FIG. 1A is administered after birth. By removing 2/3 of a left kidney of a rat aged 7 weeks and wholly removing a right kidney of a rat aged 8 weeks, the 5/6 nephrectomized rat model of the present experiment is obtained. Various data to be described later 4 weeks and 8 weeks later are obtained using the rat aged 8 weeks as a reference.

(2) The present embodiment: a normal feed is given for 6 weeks after birth. At the ages of 7 weeks and 8 weeks, the same surgery as that in Comparative Example was conducted to create a model. After aged 6 weeks, only a normal feed (hereinafter, also referred to as "a feed of the present embodiment" or a "solid preparation") kneaded with silicon fine particles shown in FIG. 1(b) is administered. The other conditions are the same as those in Comparative Example. In the same manner as in Comparative Example, various data to be described later 4 weeks and 8 weeks later are obtained using the rat aged 8 weeks as a reference.

Figure 9A:
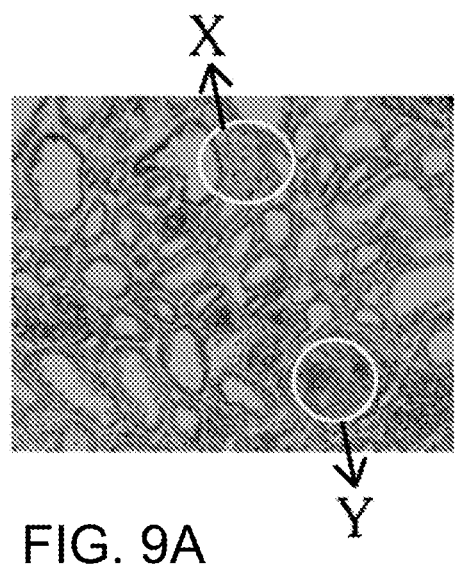
FIGS. 9A and 9B are histopathological image (HE staining) of a kidney after 4 weeks in the execution plan of FIG. 8.
Figure 9B:
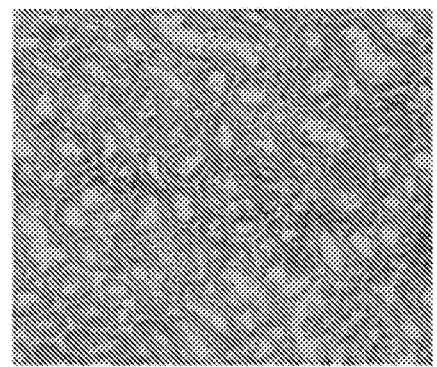

FIGS. 9A and 9B are histopathological images (HE staining) of a kidney after 4 weeks in the above-mentioned execution plan. Specifically, FIG. 9A shows a kidney of a rat ingesting a normal feed, and FIG. 9B shows a kidney of a rat ingesting a feed of the present embodiment.

FIG. 9A confirms that the symptom of chronic kidney disease is prominent. Specifically, depleted glomerulus (Y in FIG. 9A), tubule dilation that seems to be due to ischemia, and thinning of renal tubular epithelial cells were confirmed. As shown by X in FIG. 9A, renal tubulointerstitial fibrosis was also confirmed to proceed. Meanwhile, as shown in FIG. 9B, in the present embodiment, the above-mentioned findings were not recognized. This remarkable difference is considered to be caused by taking the hydrogen generated from the solid preparation taken in the body (the feed of the present embodiment) into the kidney from the following route ((A) and/or (B)) in the 5/6 nephrectomized rat model of the present embodiment.

(A) The hydrogen is taken into the blood and delivered to each organ (kidney and the like) through the bloodstream.

(B) The hydrogen having a low molecular weight passes through the mucous membrane from the intestinal tract and the like, and is directly delivered to the kidney.

As described above, such a marked difference is observed after only 4 weeks from the start of observation of the 5/6 nephrectomized rat model. This indicates that the solid preparation of the present embodiment can exhibit a high preventive effect on various symptoms of the kidney disease. This is worth noting. This remarkable difference can be said to be caused by reacting the hydroxyl radicals with the hydrogen in the intestine and/or the blood to reduce or eliminate the oxidative stress on the kidney.

Figure 10:
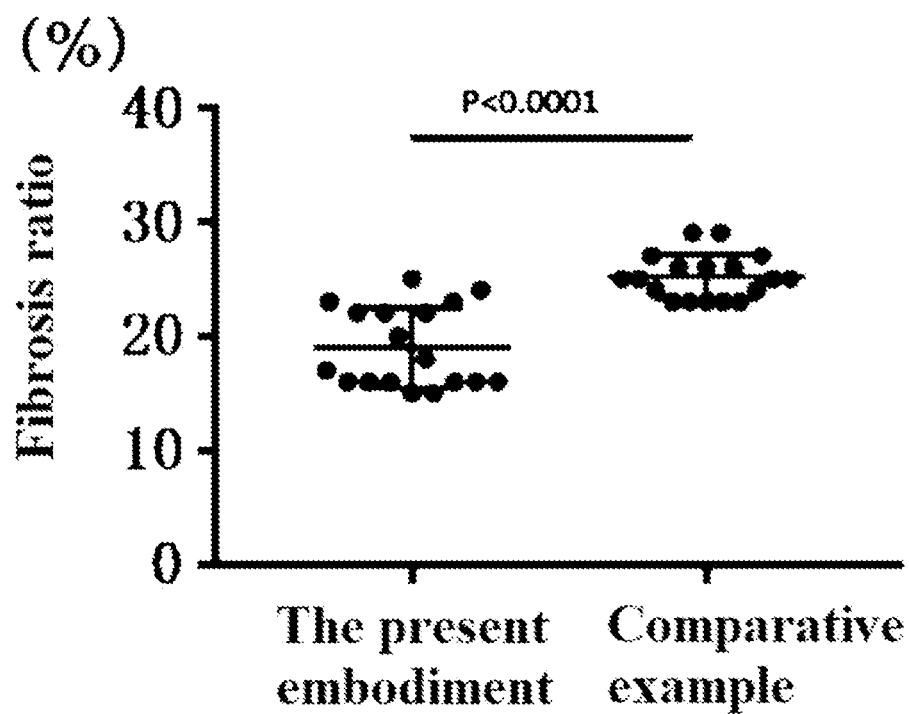
FIG. 10 is a graph showing the fibrotic conditions of renal tubular stromas of the present embodiment and Comparative Example after 4 weeks from the start of observation of a 5/6 nephrectomized rat model.

FIG. 10 is a graph showing the fibrotic conditions of renal tubular stromas of the present embodiment and Comparative Example after 4 weeks from the start of observation of a 5/6 nephrectomized rat model.

As shown in FIG. 10, the fibrosis of the renal tubular stroma was confirmed to proceed as a significant difference in the 5/6 nephrectomized rat model of Comparative Example compared with the 5/6 nephrectomized rat model of the present embodiment. Therefore, it was clarified that the fibrosis of the renal interstitium can be inhibited with high accuracy by administering the solid preparation of the present embodiment.

Figure 11:
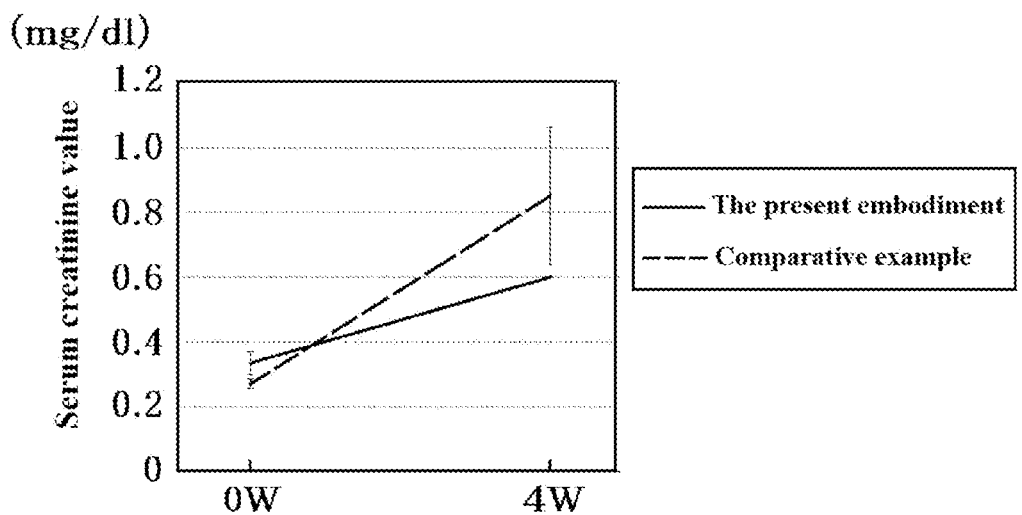
FIG. 11 is a graph showing a model creation date of a 5/6 nephrectomized rat model and serum creatinine values (mg/dl (deciliter)) of the present embodiment and Comparative Example after four weeks from the start of observation after the model is created.

FIG. 11 is a graph showing a model creation date of a 5/6 nephrectomized rat model and amounts of creatinine in serum (that is, serum creatinine values) (mg/dl (deciliter)) of the present embodiment and Comparative Example after four weeks from the start of observation after the model is created.

As shown in FIG. 11, the increase in the amount of creatinine in serum was confirmed to be inhibited in the 5/6 nephrectomized rat model of the present embodiment compared with the 5/6 nephrectomized rat model of Comparative Example. The slight increase in the creatinine value in the 5/6 nephrectomized rat model of the present embodiment is presumed to be due to the increase in the body weight. Therefore, it was clarified that the administration of the solid preparation of the present embodiment exhibits the effect of inhibiting the deterioration in the renal function or maintaining the renal function (typically, the effect of inhibiting the progression of chronic renal failure), or the effect of improving the renal function.

As described above, it was clarified that the significant difference between the 5/6 nephrectomized rat model of Comparative Example and the 5/6 nephrectomized rat model of the present embodiment can confirmed, whereby the solid preparation of the present embodiment can largely contribute to the effect of inhibiting the deterioration in the renal function or retaining the renal function (typically, the effect of inhibiting the progression of the chronic renal failure) or the effect of improving the renal function. Therefore, as a result of attaining reduction or elimination of the hydroxyl radicals in the body by the hydrogen produced from the silicon fine particles or the aggregates thereof contained in the drug (solid preparation) of the present embodiment, the preventive effect of the disease of kidney is considered to be obtained.

<Experiment for Confirming Reproducibility of Preventive Effect on Chronic Renal Failure>

The present inventors conducted the following experiment in order to confirm the reproducibility of the above-mentioned preventive effect on the chronic renal failure.

As a confirmation experiment, the present inventors analyzed the result of a serum creatinine value and the result of an amount of urine protein excreted when a 5/6 nephrectomized rat model aged 8 weeks is caused to ingest a normal feed or a solid preparation (feed) for 8 weeks, as in the above-mentioned Example 4. A rat model to which only a normal feed was given was used as Comparative Example.

The solid preparation (feed) employed in the confirmation experiment contains not only the solid preparation (feed) in which the content rate of silicon fine particles (and/or crystal grains of silicon) of the above-mentioned present embodiment is 2.5 wt % but also the solid preparation (feed) having each of the content rates of 0.1 wt %, 0.5 wt %, and 1.0 wt %. The production method for the above-mentioned solid preparation (feed) having each of the content rates is the same as that described in the first embodiment.

Figure 12:
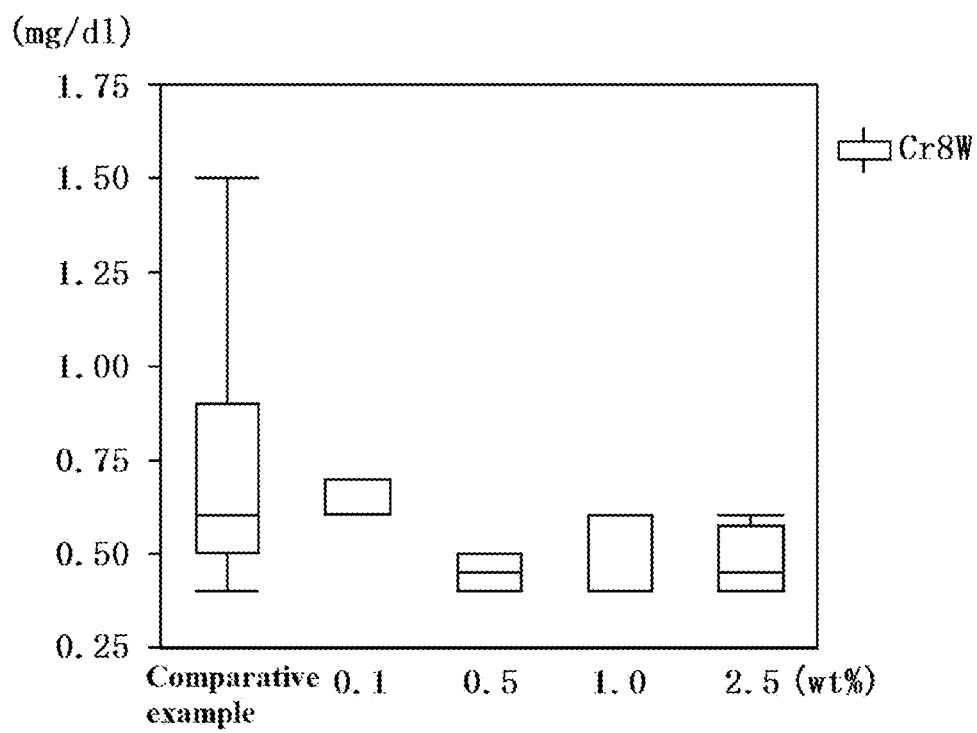
FIG. 12 is a graph showing the results of serum creatinine values for confirming the reproducibility of a preventive effect on chronic renal failure.
Figure 13:
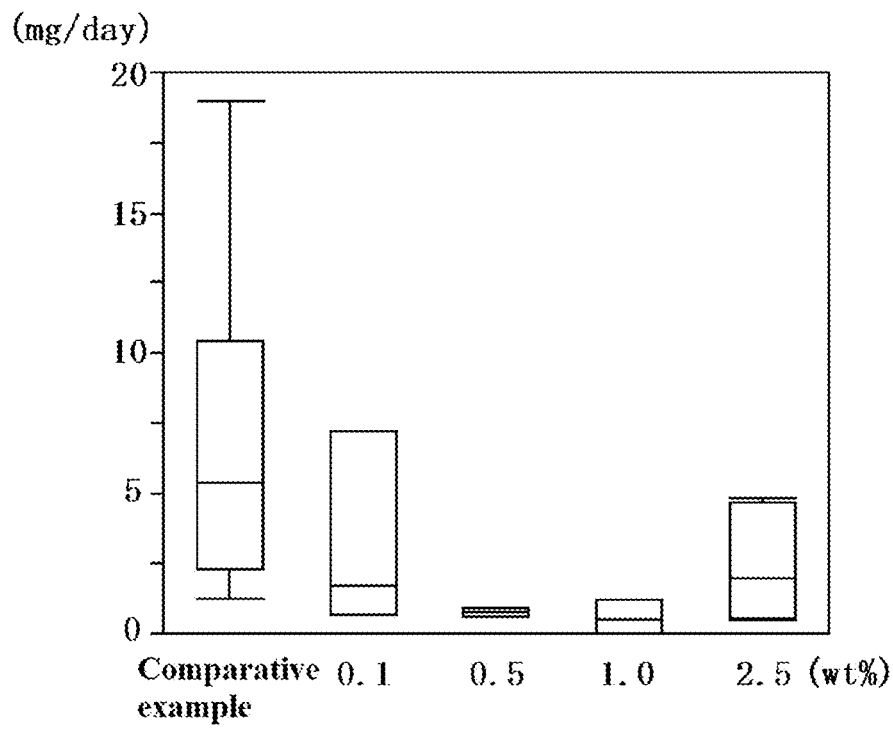
FIG. 13 is a graph showing the results of amounts of urine protein excreted for confirming the reproducibility of a preventive effect on chronic renal failure.

FIG. 12 is a graph showing the results of serum creatinine values. FIG. 13 is a graph showing the results of amounts of urine protein excreted. "The present embodiment" in FIGS. 12 and 13 contains a solid preparation (feed) in which the content rate of silicon fine particles (and/or crystal grains of silicon) is 0.1 wt %, 0.5 wt %, 1.0 wt %, and 2.5 wt %.

As shown in FIGS. 12 and 13, the significant difference between the 5/6 nephrectomized rat model of Comparative Example and the 5/6 nephrectomized rat model of the present embodiment can confirmed regardless of the content rate of the silicon fine particles (and/or the crystal grains of silicon), whereby it can be confirmed that the above-mentioned solid preparation (feed) can largely contribute to the effect of inhibiting the deterioration in the renal function or retaining the renal function (typically, the effect of inhibiting the progression of the chronic renal failure) or the effect of improving the renal function.

<Experiment for confirming Reproducibility of Preventive Effect on Acute Renal Failure>

The present inventors conducted the following experiment in order to confirm the reproducibility of the above-mentioned preventive effect on acute renal failure.

As a confirmation experiment, the present inventors started administration of a normal feed or a solid preparation (feed) to a rat aged 7 weeks. After the start of the administration, arteries and veins in a left kidney of a rat aged 8 weeks were blocked. After 60 minutes, the blocking was released and a right kidney was removed. Under these conditions, the results of serum creatinine values after 24 hours and 72 hours from the release of the blocking, and the result of an amount of urine protein excreted after 24 hours were analyzed. A rat model to which only a normal feed was given was used as Comparative Example.

Figure 14:
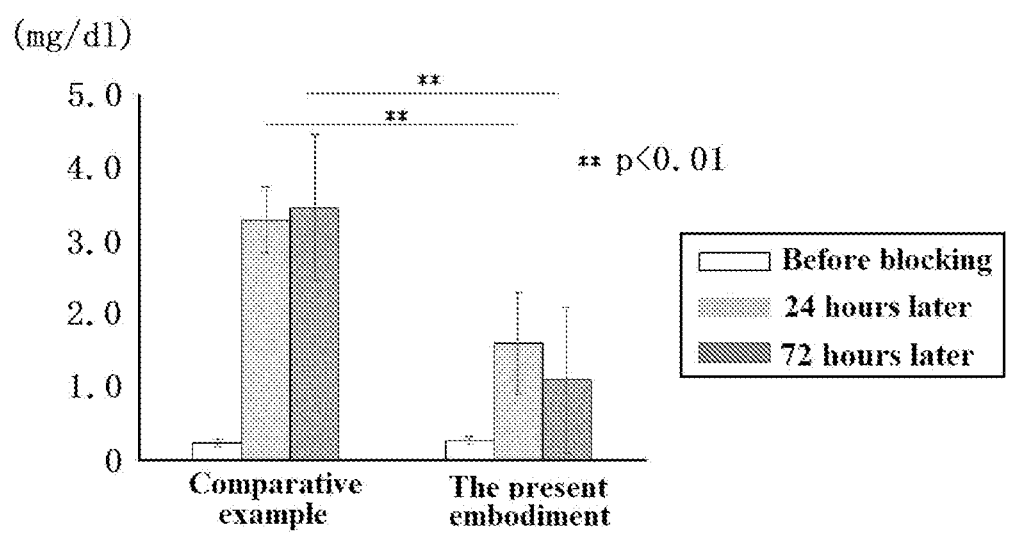
FIG. 14 is a graph showing the results of serum creatinine values for confirming the reproducibility of a preventive effect on acute renal failure.
Figure 15:
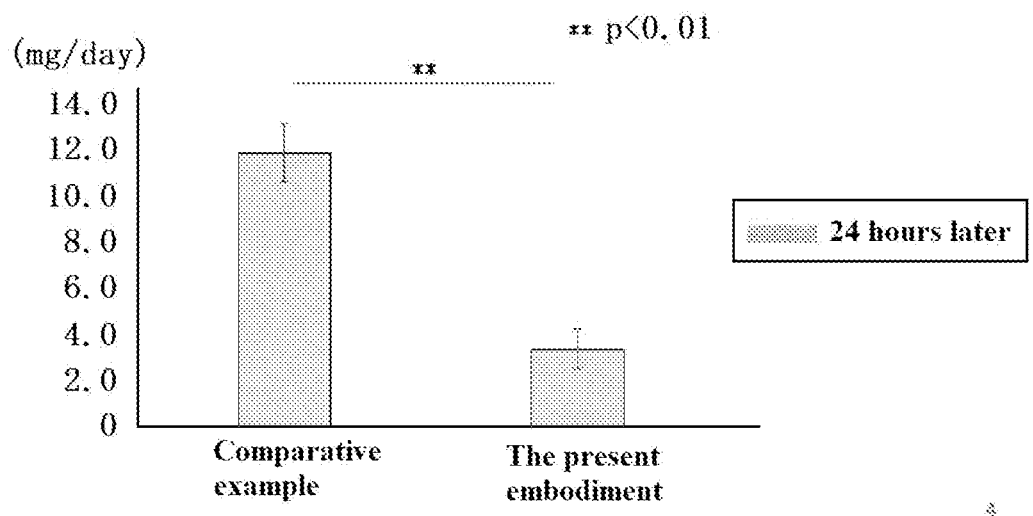
FIG. 15 is a graph showing the results of amounts of urine protein excreted for confirming the reproducibility of a preventive effect on acute renal failure.

FIG. 14 is a graph showing the results of serum creatinine values. FIG. 15 is a graph showing the results of amounts of urine protein excreted.

The solid preparation (feed) employed in the confirmation experiment is a solid preparation (feed) in which the content rate of silicon fine particles (and/or crystal grains of silicon) in the above-mentioned present embodiment is 2.5 wt %. The production method for the solid preparation (feed) is the same as that described in the first embodiment.

As shown in FIGS. 14 and 15, the significant difference between the acute renal failure rat model of the present embodiment to which the silicon fine particles (and/or crystal grains of silicon) is administered and the acute renal failure rat model of Comparative Example could be confirmed. Therefore, it could be confirmed that the above-mentioned solid preparation (feed) can largely contribute to the effect of inhibiting the deterioration in the renal function or maintaining the renal function (typically, the effect of inhibiting the progression of chronic renal failure), or the effect of improving the renal function.

As described so far, the solid preparation of each of the above-mentioned embodiments (including Modified Examples) is a drug for a disease of kidney. The drug is typically a drug for chronic renal failure, but the target disease in which the pharmacological effect of the solid preparation of each of the above-mentioned embodiments (including Modified Examples) is obtained is not limited to the chronic renal failure. For example, for at least one renal disease selected from the group of renal fibrosis, acute kidney injury, renal ischemia reperfusion injury, drug-induced renal dysfunction, and chronic kidney disease, the solid preparations of the above-mentioned embodiments (including Modified Examples) can function as a drug.

Second Embodiment

In the present embodiment, a confirmation experiment was conducted for the therapeutic effect of a solid preparation 100 as an example of the "drug" of the first embodiment using the 5/6 nephrectomized rat model described in Example 4.

Figure 16:
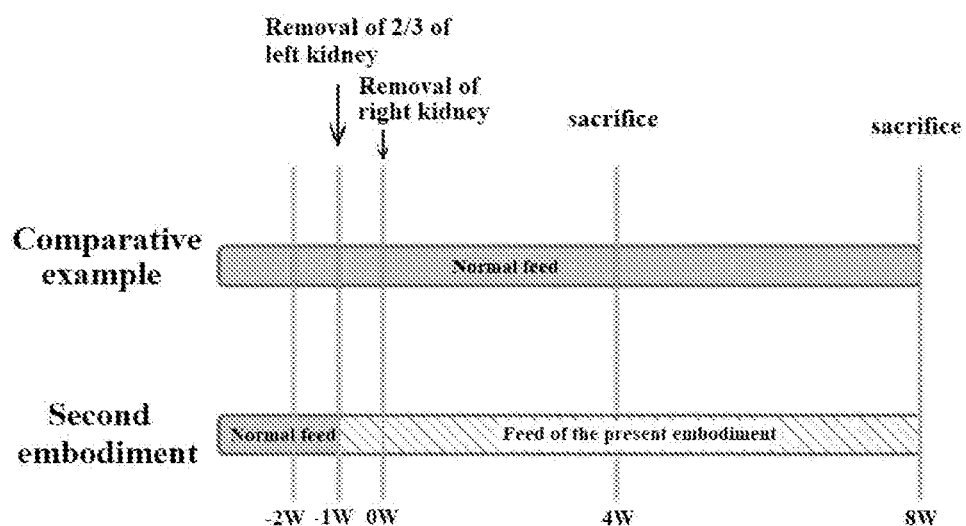
FIG. 16 is an execution plan (protocol) for confirming the therapeutic effect of a solid preparation of a second embodiment using a 5/6 nephrectomized rat model.

FIG. 16 is an execution plan (protocol) for confirming the therapeutic effect of the solid preparation of the first embodiment (containing 2.5 wt % of silicon fine particles (and/or crystal grains of silicon)) using a 5/6 nephrectomized rat model. Descriptions overlapping with those in the first embodiment may be omitted. In the present embodiment, a model is created by conducting the same surgery as that in the first embodiment at the age of 7 weeks and 8 weeks. After the age of 7 weeks, only a normal feed kneaded with silicon fine particles shown in FIG. 1(b) (hereinafter, also referred to as a "feed of the present embodiment" or a "solid preparation") is administered.

Also in the present embodiment, the usefulness from the viewpoint of the treatment of kidney disease is confirmed.

As described above, also from the viewpoint of the treatment of kidney disease, the significant difference between the 5/6 nephrectomized rat model of Comparative Example and the 5/6 nephrectomized rat model of the present embodiment is confirmed, whereby the solid preparation of the present embodiment can largely contribute to the effect of inhibiting the deterioration in the renal function or maintaining the renal function (typically, the effect of inhibiting the progression of chronic renal failure), or the effect of improving the renal function. Therefore, by attaining reduction or elimination of hydroxyl radicals in the body by hydrogen generated from silicon fine particles or aggregates thereof contained in the drug (solid preparation) of the present embodiment, a therapeutic effect on the disease of kidney can be exhibited.

Also in the present embodiment, the above-mentioned solid preparation is a drug for disease of kidney. Also from the viewpoint of the treatment of the kidney disease, the drug is typically a drug for chronic renal failure, but the target disease in which the pharmacological effect of the solid preparation of the present embodiment is obtained is limited to chronic renal failure. For example, for at least one renal disease selected from the group of renal fibrosis, acute kidney injury, renal ischemia reperfusion injury, drug-induced renal dysfunction, and chronic kidney disease, the solid preparation of the present embodiment can function as a drug.

<Experiment for Confirming Reproducibility of Treatment Effect on Chronic Renal Failure>

The present inventors conducted the following experiment in order to confirm the reproducibility of the above-mentioned therapeutic effect on chronic renal failure.

As a confirmation experiment, the present inventors removed 2/3 of a left kidney of a rat aged 7 weeks and started administration of a normal feed or a solid preparation (feed). The results of a serum creatinine value and an amount of urine protein excreted were analyzed when a right kidney of a rat aged 8 weeks after the start of the administration was completely removed. Using the rat aged 8 weeks as a reference, various data described later 4 weeks and 8 weeks later were obtained. A rat model to which only a normal feed was given was used as Comparative Example.

The solid preparation (feed) employed in the confirmation experiment contains not only the solid preparation (feed) in which the content rate of silicon fine particles (and/or crystal grains of silicon) of the above-mentioned present embodiment is 2.5 wt % but also the solid preparation (feed) having each of the content rates of 0.1 wt %, wt %, and 1.0 wt %. The production method for the above-mentioned solid preparation (feed) having each of the content rates is the same as that described in the first embodiment.

Figure 17:
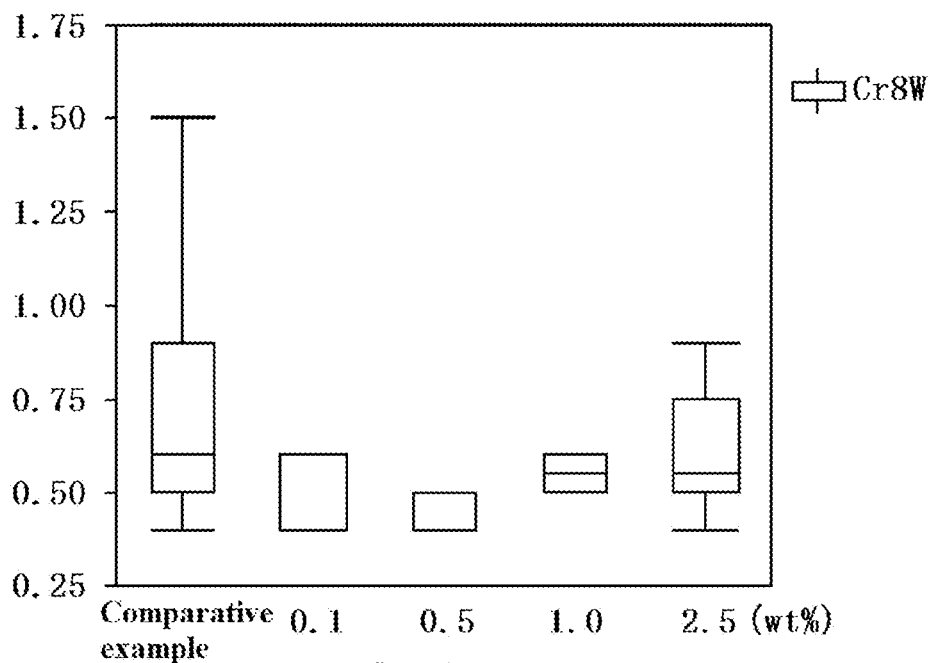
FIG. 17 is a graph showing the results of serum creatinine values for confirming the reproducibility of a therapeutic effect on chronic renal failure.
Figure 18:
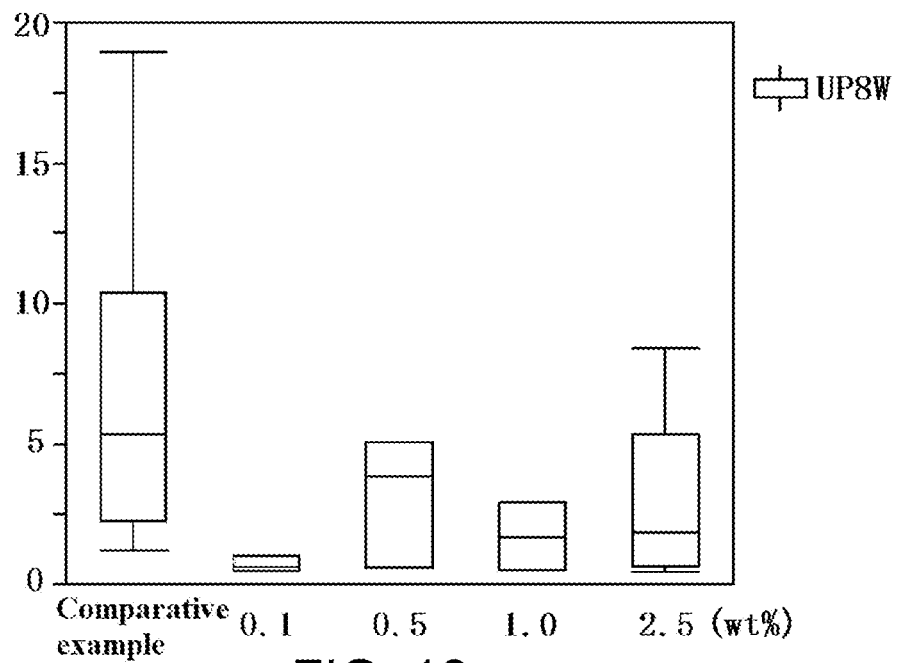
FIG. 18 is a graph showing the results of amounts of urine protein excreted for confirming the reproducibility of a therapeutic effect on chronic renal failure.

FIG. 17 is a graph showing the results of serum creatinine values. FIG. 18 is a graph showing the results of amounts of urine protein excreted. The "present embodiment" in FIGS. 17 and 18 contains a solid preparation (feed) in which the content rate of silicon fine particles (and/or crystal grains of silicon) is 0.1 wt %, 0.5 wt %, 1.0 wt %, and 2.5 wt %.

As shown in FIGS. 17 and 18, regardless of the content rate of the silicon fine particles (and/or crystal grains of silicon), a significant difference between a chronic renal failure rat model to which a normal feed already in an exacerbation state is administered (Comparative Example) and a chronic renal failure rat model in the present embodiment could be confirmed. Therefore, it could be confirmed that the above-mentioned solid preparation (feed) can largely contribute to the effect of inhibiting the deterioration in the renal function, retaining the renal function, or curing a deteriorated renal function (or relieving the renal function) (typically, the effect of inhibiting the progression of chronic renal failure, and the effect of curing the chronic renal failure) or the effect of improving the renal function.

Other Embodiments

One aspect of the production method for silicon fine particles in the above-mentioned drug (solid preparation) includes a step of finely dividing a silicon particle having a crystal grain diameter of more than 1 μm by a physical grinding method to form silicon fine particles mainly having a crystallite diameter of 1 nm or more and 100 nm or less. A suitable example of the physical grinding method is a method for grinding a silicon particle by a bead mill grinding method, a planetary ball mill grinding method, a shock wave grinding method, a high-pressure collision method, a jet mill grinding method, or a combination of two or more thereof. It is also possible to employ known chemical methods. From the viewpoint of production costs or ease of production control, a particularly suitable example is only a bead mill grinding method or a grinding method including at least a bead mill grinding method.

The above-mentioned embodiments employ, as a starting material, silicon particles, i.e., a commercially available high-purity silicon panicle powder. The starting material, however, is not limited to such silicon particles.

As one suitable aspect, the employment of porous crystal grains having nano-order voids together with or in place of the "aggregates" in each of the above-described embodiments can attain the use of particles having a large overall diameter and/or particles having a large surface area. For example, the silicon fine particle of each of the above-mentioned embodiments does not pass through a cell membrane of the intestinal tract and between cells of the intestinal tract; the aggregate of the silicon fine particles does not pass through the cell membrane and between the cells; or the crystal grain of silicon in each of the above-described embodiments does not pass through the cell membrane and between the cells. This is one suitable aspect from the viewpoint of securing the safety of each of the above-mentioned embodiments with higher accuracy.

In humans and non-human animals, one of causes for efficiently generating hydrogen from the silicon fine particles of each of the above-mentioned embodiments is considered to be a mildly alkaline intestinal fluid. Therefore, in each of the above-mentioned embodiments, in order to support the attainment of the mildly alkaline, for example, a mixture obtained by previously mixing the silicon fine particles with a bicarbonate such as sodium bicarbonate or potassium bicarbonate is administered as one of effective methods. In this case, it is preferable that the bicarbonate is decomposed by, for example, human stomach acid, so that the mixture is protected from the stomach acid to cause the mixture to serve as an enteric coating agent for dissolution in the intestine. Therefore, as one suitable aspect, the administration method is the oral administration of the enteric coating agent containing the silicon fine particle, the aggregate of the silicon fine particles or the crystal grain of silicon having a hydrogen-generating ability and the bicarbonate in each of the above-mentioned embodiments.

The disclosure of the above-mentioned embodiments or Examples is intended for describing the embodiments and is not intended for limiting the present invention. In addition, Modified Examples within the scope of the present invention, including other combinations of the embodiments and Examples, are also included in the scope of claims.

INDUSTRIAL APPLICABILITY

A drug of the present invention and a production method therefor (including a production method for a substance of the drug) can be widely utilized in a medical industry, a medical drug industry, and a health industry.

The invention claimed is:

1. A drug for a disease of a kidney, comprising one or more of (a), (b) or (c):
   (a) an aggregate of silicon fine particles, the aggregate having a size of more than 0.1 μm;

(b) a crystal grain of silicon, the crystal grain having a particle size of about 1 μm to about 2 μm, and
(c) one or more hydrogen generating material selected from the group of:
   porous silicon fine particles having a size of more than 100 nm,
   polycrystalline silicon fine particles having a size of more than 100 nm,
   unfree silicon fine particles having a size of more than 100 nm,
   hardly crushed silicon fine particles having a size of more than 100 nm,
   silicon fine particles having a size of more than 100 nm and granulated with an undecomposed binding agent, and
   a porous crystal grain of silicon, the porous crystal grain having a size of more than 100 nm,
wherein hydrogen is generated by bringing a water-containing liquid in an intestine into contact with the aggregate of silicon fine particles, the crystal grain of silicon or the one or more hydrogen generating material.

2. The drug according to claim 1, wherein the disease is at least one selected from a group of renal fibrosis, acute kidney injury, renal ischemia reperfusion injury, drug-induced renal dysfunction, and chronic kidney disease.

3. The drug according to claim 1, wherein the drug is prepared to be suitable for oral ingestion.

4. The drug according to claim 1, wherein
   the aggregate of silicon fine particles does not pass through a cell membrane of an intestinal tract and between cells of the intestinal tract,
   the crystal grain of silicon does not pass through the cell membrane and between the cells, and
   the hydrogen generating material does not pass through the cell membrane and between the cells.

5. The drug according to claim 1, further comprising a pH value adjusting agent that sets a pH value of a water-containing liquid to more than 7 and less than 9 when the drug is disintegrated in pure water.

6. The drug according to claim 1, wherein the silicon fine particles include a silicon fine particle having a crystallite diameter of 1 nm or more and 100 nm or less.

7. The drug according claim 1, wherein an oxidative stress on the kidney is reduced or eliminated by reacting hydroxyl radicals with hydrogen in an intestine and/or blood.

8. The drug according to claim 2, wherein the drug is prepared to be suitable for oral ingestion.

9. The drug according to claim 2, wherein
   the aggregate of silicon fine particles does not pass through a cell membrane of an intestinal tract and between cells of the intestinal tract,
   the crystal grain of silicon does not pass through the cell membrane and between the cells, and
   the hydrogen generating material does not pass through the cell membrane and between the cells.

10. The drug according to claim 3, wherein
   the aggregate of silicon fine particles does not pass through a cell membrane of an intestinal tract and between cells of the intestinal tract,
   the crystal grain of silicon does not pass through the cell membrane and between the cells, and
   the hydrogen generating material does not pass through the cell membrane and between the cells.

11. The drug according to claim 1, wherein the drug treats the disease of the kidney by reducing renal tubulointerstitial fibrosis or a depleted glomerulus.

12. The drug according to claim 1, wherein the drug prevents the disease of the kidney by reducing renal tubulointerstitial fibrosis or a depleted glomerulus.

13. The drug according to claim 1, wherein the drug is stored in a packaged state.

14. The drug according to claim 1, further comprising an acid agent that allows adjustment to acidity of the water containing liquid to a pH of 2 or more and less than 7.

* * * * *